US010548296B2

(12) United States Patent
Markham

(10) Patent No.: US 10,548,296 B2
(45) Date of Patent: Feb. 4, 2020

(54) SYSTEM AND METHOD FOR REDUCING ANIMAL ANXIETY BY SCENT ASSOCIATION

(71) Applicant: Joseph P. Markham, Arvada, CO (US)

(72) Inventor: Joseph P. Markham, Arvada, CO (US)

(73) Assignee: Joseph P. Markham, Arvada, CO (US)

( * ) Notice: Subject to any disclaimer, the term of this patent is extended or adjusted under 35 U.S.C. 154(b) by 216 days.

(21) Appl. No.: 15/589,806

(22) Filed: May 8, 2017

(65) Prior Publication Data
US 2018/0317454 A1    Nov. 8, 2018

(51) Int. Cl.
*A01K 15/02*        (2006.01)

(52) U.S. Cl.
CPC .................... *A01K 15/02* (2013.01)

(58) Field of Classification Search
CPC ........................ A01K 15/02; A01K 15/025
USPC ........................................................ 119/712
See application file for complete search history.

(56) References Cited

U.S. PATENT DOCUMENTS

| 5,351,653 | A | * | 10/1994 | Marischen | ........... | A01K 15/021 |
| | | | | | | 119/719 |
| 6,039,688 | A | * | 3/2000 | Douglas | .............. | G06F 19/3475 |
| | | | | | | 600/300 |
| 7,146,934 | B1 | | 12/2006 | Staley | | |
| 8,028,662 | B2 | | 10/2011 | Raymond | | |
| 8,776,731 | B1 | * | 7/2014 | Curtis | .................... | A01K 15/02 |
| | | | | | | 119/712 |
| 2005/0002863 | A1 | * | 1/2005 | Araujo | ............... | A61K 49/0004 |
| | | | | | | 424/9.2 |
| 2012/0124387 | A1 | * | 5/2012 | Skocic | ................ | G06F 21/6218 |
| | | | | | | 713/186 |
| 2012/0216755 | A1 | | 8/2012 | Collins | | |
| 2013/0014706 | A1 | * | 1/2013 | Menkes | ................. | A61D 13/00 |
| | | | | | | 119/859 |

(Continued)

OTHER PUBLICATIONS

Miller, Pat; "Step-by-Step Training for Your Dog's Next Vet Visit." Whole Dog Journal. Dec. 2015. <https://www.whole-dog-journal.com/issues/18_12/features/Step-by-Step-Training-for-Your-Dogs-Next-Vet-Visit_21352-1.html> (Year: 2015).*

(Continued)

*Primary Examiner* — Magdalena Topolski
*Assistant Examiner* — Morgan T Barlow
(74) *Attorney, Agent, or Firm* — Berg Hill Greenleaf Ruscitti LLP

(57) ABSTRACT

The invention is a system and method for the reduction of stress and anxiety responses by animals to unfamiliar events or circumstances such as veterinary visits. The method includes progressive scent identification conditioning. An animal associates one or more pleasing fragrances or scents with pleasure and safety and thus a reduced level of stress/anxiety. This association persists for a sufficient period of time so the animal is able to better handle unfamiliar events/circumstances by maintaining a lower level of stress/anxiety. Scent association conditioning is achieved by presentation of a reward such as edible treats of different sizes and effective taste intensities when scent exposure occurs. The time between scent exposure and receipt of a treat is gradually increased during conditioning to reach an optimal or maximum period in which the animal can maintain a low level of stress/anxiety.

11 Claims, 2 Drawing Sheets

(56) References Cited

U.S. PATENT DOCUMENTS

| | | | |
|---|---|---|---|
| 2014/0290583 A1* | 10/2014 | Yin | A01K 5/02 |
| | | | 119/51.02 |
| 2016/0081302 A1 | 3/2016 | Hare et al. | |
| 2016/0219835 A1* | 8/2016 | Faecher | A01K 15/025 |
| 2018/0064060 A1* | 3/2018 | Romney | A01K 1/033 |
| 2018/0160652 A1* | 6/2018 | Torres | A01K 15/021 |

OTHER PUBLICATIONS

Lloyd, Janice K. F., "Minimising Stress for Patients in the Veterinary Hospital—Why It Is Important and What Can Be Done about It" Vet. Sci. 2017, 4(2), 22; <https://doi.org/10.3390/vetsci4020022> (Year: 2016).*

* cited by examiner

SYSTEM AND METHOD FOR REDUCING ANIMAL ANXIETY BY SCENT ASSOCIATION

FIELD OF THE INVENTION

The invention relates to a system and method for conditioning or altering the behavior of an animal, and more particularly, to a system and method for animal conditioning to reduce the fear and anxiety associated with stressful events or environments such as veterinary visits.

BACKGROUND OF THE INVENTION

It is well known that animals negatively react to veterinary visits. The potential pain and discomfort associated with a veterinary visit may trigger various levels of anxiety reactions by the animal. Even if an animal is not required to undergo a painful veterinary procedure, the veterinary office environment may still trigger a negative reaction by the animal which makes it more difficult for the veterinary professional to conduct even brief and simple health evaluations.

In some cases, the negative animal reactions can be significant enough that it prevents veterinary professional from effectively conducting the evaluation or procedure, and this interference degrades the quality of the veterinary visit. High anxiety reactions by an animal can also jeopardize the safety of the animal, the animal's owner who may be present and attending veterinary professionals.

It is common practice for a veterinary professional to provide an edible treat to the animal which may briefly distract the animal, but administering this treat may only provide a slight and temporary reduction in animal anxiety or distraction resulting in the animal quickly returning to its high anxiety state.

Considering the inherent problems associated with animal anxiety and veterinary visits, there is a need for a method that may substantially reduce animal anxiety associated with veterinary visits, and the method being one that is effective despite the differences associated with individual animals and their response to the unfamiliar environment of a veterinary office.

SUMMARY OF THE INVENTION

The present invention is a system and method for the reduction of fear or anxiety responses by animals to numerous situations including veterinary visits and procedures, thunderstorms, grooming, kennel stays, and others. The terms "fear" and "anxiety" are intended to generally describe animal behavior associated with physical signs of agitation manifested in increased physical movement and aggressive behavior to resist being handled during a veterinary visit or a flight behavior to escape from the veterinary office environment.

It should be understood that the invention is not limited to any particular theory regarding animal behavior and rather is directed at a system and method to produce a tangible result in the actions and reactions of the animal. In other words, while the invention may be described with respect to animal emotions, terminology that may be ascribed to a behaviorist approach to animal behavior, the system and method described herein is equally applicable to all forms of the study of animals including, without limitation, scientific, comparative and anecdotal approaches or theories.

According to one aspect of the invention, it includes a progressive or incremental scent identification by the animal for a pleasing scent or conditioning scent that corresponds to the event or environment that requires conditioning to reduce potential anxiety that the animal will exhibit when subject to the event or environment The conditioning scent achieves it purpose when combined with a reward given to the animal. The reward may take many forms such as treats given to the animal, praise, affection, and others.

Stated in another way the invention involves the use of scent conditioning by use of a distinctive and pleasing scent or smell Upon sufficient repetitive conditioning, the animal connects or associates this distinctive and pleasing scent with the event or environment resulting in reduced stress and anxiety when experiencing the event or environment.

The invention is described herein in detail with respect to a reducing animal stress or anxiety associated with a veterinary office visit. However, it shall be understood that the invention is not limited to scent conditioning for a veterinary office visit and can be applied to many other events or environments the animal may encounter.

The scent conditioning that the animal undergoes is effective for anxiety reduction during subsequent events in the future such as the next veterinary visit and subsequent visits if the animal receives scent reinforcement conditioning. As a consequence, instead of the natural fear and anxiety that is triggered with the unfamiliar and sometimes painful veterinary visit, the animal will first associate a veterinary visit with a pleasing experience.

The pleasing scent is also referred to herein as a "conditioning scent" which is a mechanism to establish a bridge or connection between the smell of the scent and a calming or settling effect on an animal. This conditioning scent provides the animal with an emotional foundation that allows the animal to overcome fear and anxiety that is more naturally associated with the veterinary visit. The conditioning scent may also be described as having a unique scent "signature" or "high note" which is intended to define a scent or fragrance that is highly distinctive to the animal; one that can be easily recalled or remembered. As mentioned, the conditioning effect that the conditioning scent can achieve is produced by the combination of the scent and a reward provided to the animal.

In tangible form, the conditioning scent can be selected fragrance(s in which the conditioning scent(s) can be applied to a broad range of objects. The conditioning scent may be applied or delivered to the objects by, but not limited to, a spray, sprit, wick, diffuser, or drops. The objects that may receive the conditioning scent include edible treats, pet toys, scratch and sniff material, or other objects that the dog does not ingest or play with such as a piece of paper or cardboard sprayed or coated with the fragrance.

The progressive or incremental scent association or scent bridge may be reinforced over time by various other forms of rewards or stimulus such as calming or reinforcing behavior exhibited by the animal owner.

The rewards provided by the owner as treats may be referred to as "home treats" or "owner treats". These treats may be optionally coated or sprayed with the conditioning scent.

In another way to describe the conditioning scent as it applies to the system and method of the invention, the use of the conditioning scent can be described within the context of a scent-reward cycle in which the animal is exposed to the selected conditioning scent and then the animal has an expectation of a pleasing reward. This scent will trigger a sense of contentment or calm for the animal as the animal becomes conditioned over time. According to another feature of the invention, one object is to increase the time between scent exposure and receipt of the reward by the animal so there is a prolonged state of contentment or calm experienced by the animal. Gradually changing the frequency of conducting scent-reward cycle conditioning along with extending the time between scent exposure and receipt of the reward within a cycle contributes to the animal developing an extended or prolonged state of contentment. According to one preferred embodiment of a method of the invention, an animal such as a dog is exposed to a treatment regimen in which a pleasing scent or conditioning scent is provided to the animal well in advance of a veterinary visit. This initial exposure to the conditioning scent can be provided to a puppy early on and weeks or months prior to a first veterinary visit. This early exposure is coupled with the provision of a reward each time.

The animal is exposed numerous times to the conditioning scent along with a corresponding reward over time. The repeated or incremental exposure can be supplemented with or owner praise and affection; either or both of which may be referred to as supplemental rewards or supplemental reinforcements. For a puppy, these initial conditioning steps can be conducted over a period of weeks or months so that the puppy will begin to associate the pleasing olfactory and taste experiences as a safe and rewarding memory.

Another step in the method is to make one or more visits to the veterinary office environment to expose the animal to the environment and without undergoing an examination or procedure. Stated in another way, these initial visits to the veterinary office can be viewed as "trial runs" in which the animal is able to process the new environmental factors in the veterinary office and be further rewarded by receiving a special or "high value" treat in the office, an "enhanced" conditioning scent, and additional praise or affection not only from the owner but also from veterinary personnel. These three behavior enhancers may be provided in any combination, all three not being required according to the method of the invention.

For the praise or affection, this may include physical contact with the animal by petting or brushing the animal. One particular animal brush that has proven effective for grooming is the Zoom Groom® series of brushes.

The special or high value treat received at the veterinary office is one which may have a particularly bold taste and/or smell that is pleasing to the animal. The high value treat is therefore intended to create a memory in the animal which is at a higher level or more intense level than the home treats provided to the animal prior to the veterinary visits. Similar to the high value treat, the enhanced conditioning scent is one that includes the pleasing scent provided to the animal prior to the veterinary visit, but has an increased scent concentration, and may optionally include additional pleasing scents or combination of pleasing scents.

Another step in the method is to conduct intermediate behavior reinforcement by continuing to expose the animal to the conditioning scent and reward, and optionally to the supplemental rewards. The frequency of these intermediate conditioning acts or events can be a few occurrences per week which has shown to cause an animal such as a dog to maintain a sufficient level of memory.

Another step in the method is for the veterinary office to send scheduled veterinary office visit reminders with one or more mailings that include the preferred conditioning scent and/or a smaller portion size of the high value treat. This reminder(s) serve not only to further reinforce an animal's prior conditioning, but also to remind the owner that the animal should be undergoing continued reinforcement with the conditioning scent.

A next step in the method includes conducting an actual veterinary office visit in which the animal is exposed to the conditioning scent and reward at some time shortly before the visit, such as during travel to the veterinary office or just prior to the travel assuming the travel time is within an hour or thereabouts.

When the animal arrives for the actual office visit, the animal is provided with the enhanced conditioning scent along with the high value treat. The conditioning scent may be incorporated within the high value treat, or the high value treat can be separated from the conditioning scent. The owner and/or veterinary personnel may also supplement the office visit with praise and affection.

As the veterinary personnel conduct their tasks during the visit, the animal will exhibit a lower level of anxiety or stress, which may greatly enhance the quality of the office visit for all involved. At the end of the office visit, the animal may again be provided with the conditioning scent and/or another high value treat.

Post veterinary office visit reinforcement should be conducted to continue to reinforce with the animal the pleasing scent and/or taste associated with the veterinary office environment.

Therefore, it should be apparent that the method of the invention includes a plurality of incremental steps or actions that take place in order to condition the animal to inherently adopt a more calm and settled emotional state when in the veterinary office environment.

According to a system of the invention, it includes at least one selected conditioning scent, home treats, high value treats, and occurrences of owner attention and/or affection. These elements of the system are incrementally executed at preselected times to most optimally reinforce animal behavior in anticipation of one or more veterinary office visits.

The method and system of the invention provide a conditioning scent that contains a unique scent signature or high note that is easily identified and remembered by an animal. The conditioning scent may be delivered through various means and therefore incorporated in or on many different types of objects.

The exposure of the conditioning scent to the animal is paired with a reward. Early conditioning is preferably always paired with a treat reward given to the animal within a short period of time or immediately after exposure to the scent. Supplemental rewards may include praise, affection, and toys given to the animal. As the animal shows progress in conditioning, the animal caregivers who are providing the conditioning may gradually increase the time between exposure to the scent and delivery of the rewards. The increased time in between exposure to the conditioning scent and the delivery of the reward will measurably reduce stress and anxiety of the animal therefore resulting in a prolonged state of relative calm or reduced stress/anxiety for the animal. Accordingly, the prolonged state of reduced stress/anxiety provides the animal with a behavioral solution to an otherwise stressful circumstance or event in which the animal would otherwise succumb to its natural instinct to generate adrenaline and/or other fight or flight responses.

According to another feature of the invention, the conditioning scent can be selected to be a single or universal scent meaning the scent used is not changed over time; however the strength or intensity of the scent may be altered. According to one preferred embodiment, the use of a consistent universal scent coupled or paired with a high value treat may provide the optimal stimulus for the animal to maintain a high level of retention and a prolonged state of reduced stress or anxiety.

Considering the above features and attributes of the invention, in one aspect, it may be considered a method of reducing stress and anxiety for an animal during a veterinary visit, said method comprising: selecting one or more conditioning scents; introducing at least one conditioning scent to an animal along with a reward; repeatedly exposing the animal to the at least one conditioning scent along with a reward; conducting a trial run visit to a veterinary office in which the animal receives conditioning scent validation at the veterinary office along with receiving a reward; conducting intermediate reinforcement by subsequently exposing the at least one conditioning scent to the animal along with a reward; receiving at least one veterinary office reminder including a conditioning scent incorporated thereon; conducting a conditioning scent exposure immediately prior to a veterinary office visit; and conducting a veterinary office visit in which the animal receives an enhanced conditioning scent validation with a high value reward.

Optional features of this first aspect may further include: providing supplemental reinforcement to the animal prior to the veterinary office visit, said supplemental reinforcement including at least one of providing toys, praise or affection; one or more conditioning scents further includes a trial and error step in which a plurality of scents are provided to an animal and reactions by the animal to the plurality of scents are categorized for levels of response by the animal; providing the animal a home treat prior to the veterinary office visit and providing the animal a high value treat during the veterinary office visit wherein the home treat is of a first taste intensity and the high value treat is a second higher taste intensity; wherein the conditioning scent provided to the animal prior to the veterinary visit has a fragrance of a first intensity and the conditioning scent provided to the animal during the veterinary visit has a fragrance of a second higher intensity; and wherein said one or more conditioning scents are fragrances including at least one of anise, chamomile, lavender, tea tree, rose, vanilla, or food aromas including bacon, hotdogs, or other meat products.

Further optional features of the invention may include wherein the first taste intensity and the second higher taste intensity are differentiated by providing a lower concentration of a selected active taste constituent for the first taste intensity and providing a higher concentration of the selected active taste constituent for the second higher taste intensity.

Yet further optional features of the invention may include wherein the fragrance of a first intensity and the fragrance of a second higher intensity are differentiated by providing a lower concentration of a selected active fragrance constituent for the fragrance of a first intensity and providing a higher concentration of the selected active fragrance for the second higher intensity.

According to another aspect of the invention, it may be considered a system for reducing stress and anxiety of an animal during a veterinary visit, said system comprising: a first conditioning scent having a first fragrance intensity; a first object having the least one conditioning scent applied thereto, wherein the first object is provided to the animal in initial conditioning; a reward provided to the animal at selected times when the first object is provided to the animal, said reward including a home treat; a second conditioning scent including a fragrance of said first conditioning scent but having a second greater fragrance intensity; a second object that has the second conditioning scent applied thereto, wherein the second object is provided to the animal in a vet office environment such as during a vet office visit; and a high value treat provided to the animal in the vet office visit, said high value treat having a greater taste intensity than said home treat.

According to another broader aspect of the invention not specifically applicable to a veterinary office visit or environment, it may be considered a method of reducing stress and anxiety for an animal during an event or during exposure to a particular environment, said method comprising: selecting one or more conditioning scents; introducing at least one conditioning scent to an animal along with a reward; repeatedly exposing the animal to the at least one conditioning scent over a period of time along with the reward; conducting a trial run visit to the particular environment or conducting a trial event in which the animal receives a first conditioning scent validation at the particular environment or event along with receiving another reward; conduct intermediate reinforcement by subsequently exposing the at least one conditioning scent to the animal and providing corresponding rewards during the subsequent exposures; and conduct a live exposure to a particular environment or event in which the animal receives an enhanced second conditioning scent validation along with a high value reward.

DETAILED DESCRIPTION OF THE DRAWINGS

Figure 1:
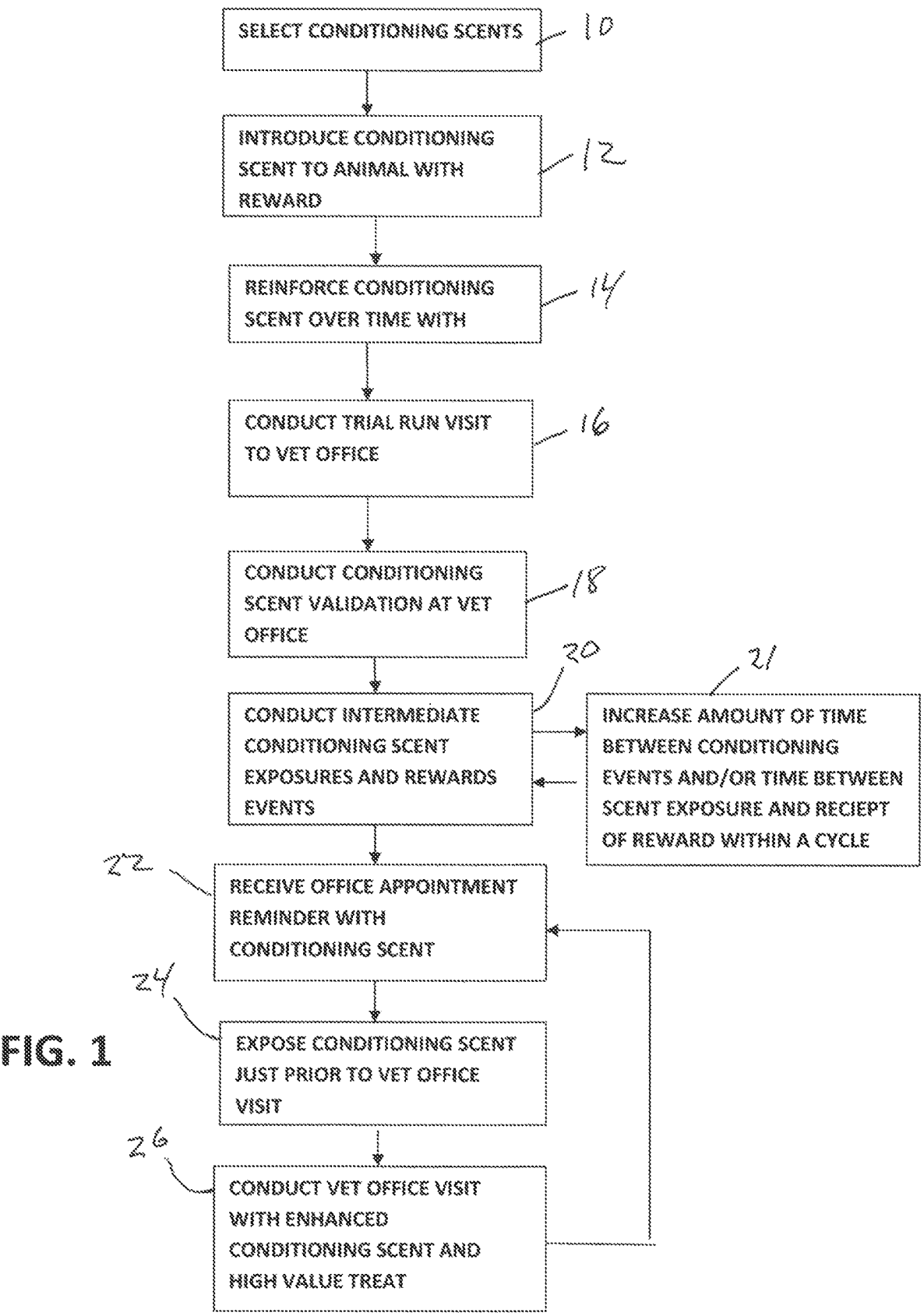
FIG. 1 is a flow chart showing steps in the method of the invention according to one preferred embodiment.

FIG. 1 shows a flow diagram describing a preferred embodiment of the method of the invention. The method is described with steps or actions to perform the method. A first step is to select conditioning scents 10. In general terms, the conditioning scents are pleasing scents or fragrances to an animal. Examples of such fragrances may include anise, chamomile, lavender, tea tree, rose, vanilla, or food aromas including bacon, hotdogs, or other meat products.

and others. An object for selecting a conditioning scent is one which will capture the attention of the animal and be remembered by the animal. The olfactory sense of animals such as dogs is highly developed and it is known that dogs are able to remember or recall specific scents.

The conditioning scent selected can be a single or universal scent meaning the scent used is not changed over time; however the strength or intensity of the scent may be altered.

A next step in the method is to introduce the desired conditioning scent(s) to the animal, shown at step 12. Introducing a conditioning scent to a puppy provides an advantage in that as the puppy grows, this unique conditioning scent is one which the animal will remember as being associated with a pleasant experience. The conditioning scent is coupled with the provision of a reward, and the reward may include edible treats or other animal food.

At step 14, a next step in the method is to reinforce the conditioning scent(s) with the animal over a period of time. There is no exact required frequency for reinforcing the conditioning scent, but conducting the reinforcing conditioning at least a few days per week over a period of weeks or months is adequate for many animals to associate the scent with a pleasant event or experience. The reinforcing conditioning is coupled with the provision of a reward, and the animal over time will directly associate the conditioning event with the reward; a pleasing outcome when the conditioning scent is present.

At step 16, a next step in the method is to conduct one or more trial runs in a visit to the veterinary office. This step involves first reinforcing the scent by exposure to the animal just prior to the trial visit, such as during travel to the veterinary office. A reward is provided to the animal when the scent exposure takes place.

At step 18, once the animal arrives at the veterinary office, the animal is exposed to the conditioning scent as a validation that the veterinary office is a safe location. One or more of the veterinary personnel may wear a glove or have another object on their person which has the selected conditioning scent for the animal. This scent association may become stronger as the animal again experiences a pleasing event that specifically occurs at the veterinary office. The animal receives the high value treat at the veterinary office as further reinforcement that the conditioning scent is to be directly associated with a pleasing outcome.

While at the veterinary office, the animal may be allowed to investigate the veterinary surroundings for sight, smell, and sound. Optionally, veterinary personnel may provide supplemental rewards such as toys, praise and affection. The animal may be taken to an examination room or other locations in the veterinary office for the animal to further investigate to confirm the veterinary office is not a location that should be feared.

While a single trial run visit may be adequate for some animals to fully gain the connection or association for the veterinary office as a safe location, conducting more than one trial run visit may be optimal.

At step 20, intermediate conditioning or reinforcement is conducted by continuing to expose the animal to the conditioning scent along with a reward including, a home treat, and attention/affection, or a combination thereof. This intermediate or interval reinforcement is conducted to enable the animal to remember the conditioning scent in preparation for a next veterinary office visit.

The use of the conditioning scent can be described within the context of a scent-reward cycle in which the animal is exposed to the selected conditioning scent and then the animal has an expectation of a pleasing reward. This scent will trigger a sense of contentment or calm for the animal as the animal becomes conditioned over time. According to another feature of the invention, one object is to increase the time between scent exposure and receipt of the reward by the animal so there is a prolonged state of contentment or calm experienced by the animal. Gradually extending the frequency of conducting scent-reward cycle conditioning and/or extending the time between scent exposure and receipt of the reward within a single cycle contributes to the animal developing an extended or prolonged state of contentment. The objective for this step is to increase the time between scent exposure and receipt of the reward by the animal so there is a prolonged state of contentment or calm experienced by the animal. This prolonged state then becomes very useful in keeping the animal calm a sufficient amount of time during an event such as a veterinary visit. Stated in another way, the time between scent exposure and receipt of a treat is gradually increased during conditioning to reach an optimal or maximum period in which the animal can maintain a low level of stress/anxiety.

Considering the scent-reward cycle, an optional step in the method is shown at step 21, namely, increasing the amount of time between conditioning events and/or the time between scent exposure and receipt of a reward within a cycle. Although step 21 is shown occurring in conjunction with the intermediate conditioning step 20, it should be understood that this step can also be conducted at any other time in the method, such as during step 14 with initial reinforcing conditioning.

At step 22, at some point in time between veterinary office visits, the veterinary office or a service associated with the veterinary office sends a reminder to the animal owner regarding the next scheduled veterinary visit. This reminder can be in the form of a mailing in which the mailing is impregnated or coated with the animal's conditioning scent. A smaller sized high value treat may also accompany the mailing. The purpose of this step is again to further reinforce the conditioning scent with the animal. This mailing also serves to remind the animal owner to continue interval or intermediate conditioning.

At step 26 a first veterinary office visit or "live" visit is conducted in which the animal will undergo an examination and/or procedure. When the animal arrives at the office, veterinary personnel will expose the animal to the conditioning scent, such as by a glove which is sprayed or coated with the conditioning scent, and the animal will receive a high value treat. At this point in the method, success is achieved if the animal exhibits an observably lower level of anxiety or stress as compared to non-conditioned animals, or as compared to when the animal had a prior veterinary visit without the conditioning scent conditioning.

After the visit is completed, the animal owner may continue to conduct intermediate conditioning from step 20, facilitate receipt of the veterinary office reminder from step 22, and conduct conditioning scent exposure just prior to the veterinary office visit from step 24. This part of the method may be repeated over and over as the animal continues to make periodic veterinary office visits during the lifetime of the animal.

Figure 2:
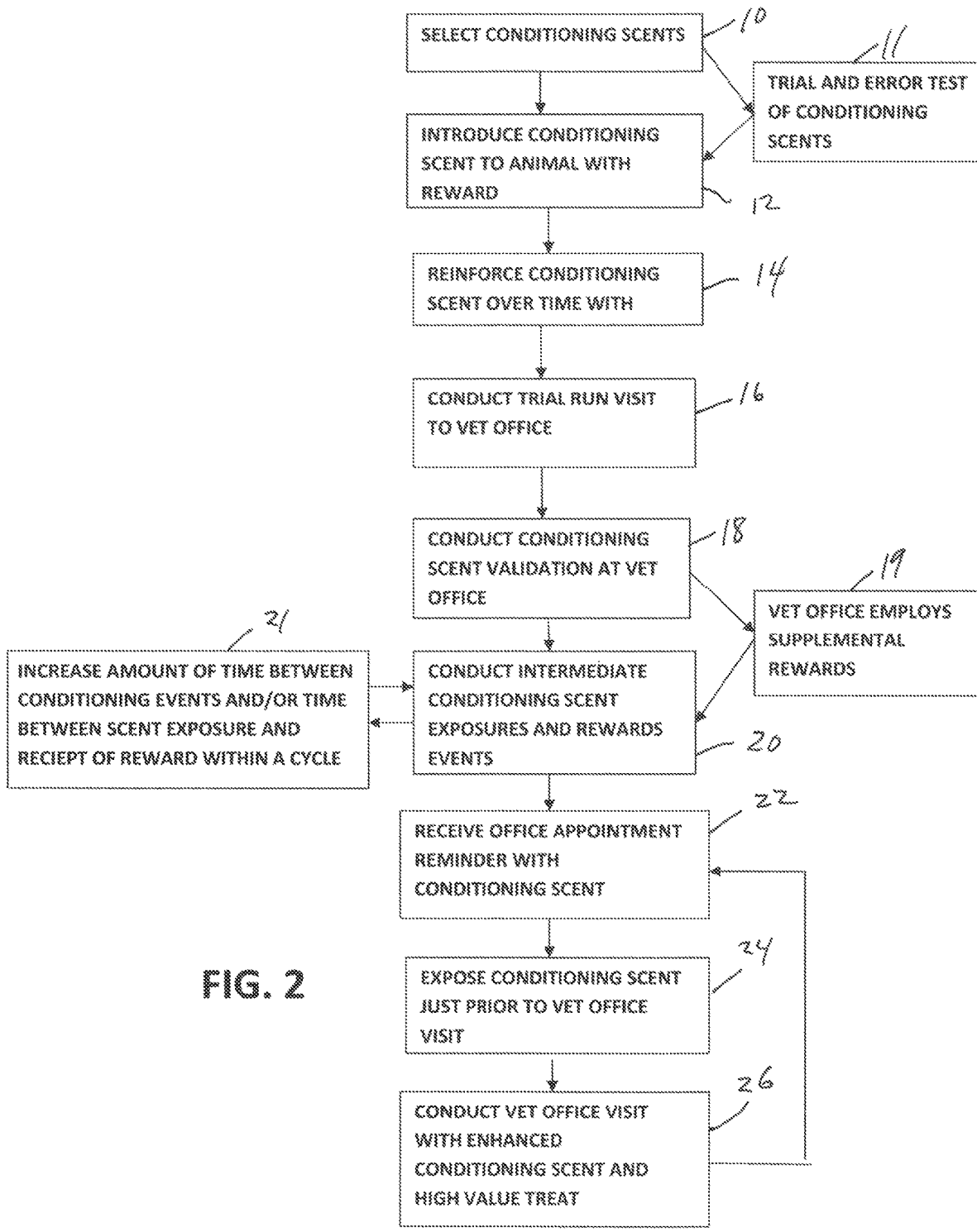
FIG. 2 is another flow chart showing steps in the method according to another embodiment.

Referring to FIG. 2, another preferred embodiment of the method of the invention is illustrated in a flow diagram. The same reference numerals used in the steps of the method correspond to the same steps as described with respect to the preferred embodiment of FIG. 1. For this additional embodiment, additional steps are provided as described below.

At step 11, trial and error testing of conditioning scents is conducted in which the animal owner determines which particular scent or group of scents best stimulate the animal. An object at this stage or step is selection of one or more optimal conditioning scents may facilitate a better long-term response by the animal as to creating a long-term association of the conditioning scent(s) and a positive experience.

At step 19, during the trial run visit to the veterinary office, the veterinary office may employ use of supplemental rewards including various combinations of toys, praise/affection, and greater intensity/enhanced conditioning scents. An object of this step is to make the trial run visit a sensory highlight for the animal in which more than one sense of the animal is highly stimulated to create a more intense memory experience for the animal regarding pleasure associated with the trial run visit.

According to another aspect of the invention, it may be a system including the physical items which are used to execute the method. These items include one or more fragrances that are the conditioning scents, and these fragrances are capable of being sprayed, coated, or otherwise delivered to an object given to the animal. The home treats may include edible treats commercially available or home treats that are derived by the animal owner. Similarly, the high value treats provided at the veterinary office may include commercially available treats or treats that are especially made for the veterinary office visits. The veterinary office reminder may include a paper or cardboard mailer with a conditioning scent that is sprayed or coated on the mailer, such as a scratch and sniff mailer. The mailer may also include smaller portions or sizes for the high value treats provided at the veterinary office. The provision of praise and affection may include grooming objects such as brushes in which the act of grooming represents physical affection.

There are number of advantages to the system and method of the invention. The steady, incremental exposure of one or more conditioning scents to an animal with corresponding rewards effectively conditions the animal to associate a pleasing scent with a veterinary office visit which may significantly reduce stress and anxiety associated with such visits. The highly developed olfactory sense of an animal such as a dog allows the conditioning scents to be maintained in the memory of the animal more effectively than other forms of stimulation.

The method does not involve high cost devices, and may be executed by an animal owner in conjunction with a participating veterinary office at low cost.

According to one preferred embodiment, the use of a consistent universal scent coupled or paired with a high value treat may provide the optimal stimulus for the animal to maintain a high level of retention and a prolonged state of reduced stress or anxiety.

The method and system of the invention provide a conditioning scent characterized by a unique scent signature or high note that an animal may easily identify and remember. The exposure of the conditioning scent to the animal is paired with a reward. Supplemental rewards may include praise, affection, and toys given to the animal. As the animal shows progress in conditioning, the animal caregivers may gradually increase the time between exposure to the scent and delivery of the rewards. The increased time in between exposure to the conditioning scent and the delivery of the reward will measurably reduce stress and anxiety of the animal therefore resulting in a prolonged state of relative calm or reduced stress/anxiety for the animal. The prolonged state of reduced stress/anxiety results in the animal behaving differently to an otherwise stressful circumstance or event. Without scent conditioning the animal would succumb to its natural instinct to generate adrenaline and/or other fight or flight responses. The scent conditioning according to the method and system of the invention results in the animal exhibiting a different behavior, one which results in the animal showing a lower level of stress/anxiety.

While the invention has been described with respect to one or more preferred embodiments, it shall be understood that the invention is not specifically limited to these disclosed embodiments. The scope of the invention should be fully appreciated based upon the scope of the claims appended hereto, and which may be broader than the disclosed embodiments.

What is claimed is:

1. A method of reducing stress and anxiety for an animal, said method comprising:
    selecting one or more conditioning scents;
    introducing at least one conditioning scent to an animal along with a reward;
    repeatedly exposing the animal to the at least one conditioning scent over a period of time along with the reward;
    conducting a trial run visit to a veterinary office in which the animal receives validation at the veterinary office by exposure to the at least one scent along with another reward;
    conducting intermediate reinforcement by subsequently exposing the animal to the at least one conditioning scent;
    exposing the animal again to the at least one conditioning scent prior to a subsequent veterinary office visit;
    conducting the subsequent veterinary office visit in which the animal is exposed to an enhanced conditioning scent; and
    receiving at least one veterinary office reminder including the at least one conditioning scent or the enhanced conditioning scent incorporated thereon.

2. The method, as claimed in claim 1, further including:
    providing the animal a high value treat during conducting the subsequent veterinary office visit.

3. The method, as claimed in claim 1, further including:
    providing supplemental reinforcement to the animal prior to the subsequent veterinary office visit including providing the animal with at least one of toy, praise or affection.

4. The method, as claimed in claim 1, wherein:
    the step of selecting one or more conditioning scents further includes a trial and error step in which a plurality of scents are provided to an animal and reactions by the animal to the plurality of scents are categorized for levels of response by the animal.

5. The method, as claimed in claim 1, further including:
    providing the animal a home treat prior to the subsequent veterinary office visit and providing the animal a high value treat during the subsequent veterinary office visit wherein the home treat is of a first taste intensity and the high value treat is a second higher taste intensity.

6. The method, as claimed in claim 5, wherein:
    the first taste intensity and the second higher taste intensity are differentiated by providing a lower concentration of a selected active taste constituent for the first taste intensity and providing a higher concentration of the selected active taste constituent for the second higher taste intensity.

7. The method, as claimed in claim 1, wherein the at least one conditioning scent provided to the animal prior to the trial run visit to the veterinary office has a fragrance of a first intensity and the enhanced conditioning scent provided to the animal during the subsequent veterinary visit has a fragrance of a second higher intensity.

8. The method, as claimed in claim 7, wherein:
    the fragrance of a first intensity and the fragrance of a second higher intensity are differentiated by providing a lower concentration of a selected active fragrance constituent for the fragrance of a first intensity and providing a higher concentration of the selected active fragrance for the second higher intensity.

9. The method, as claimed in claim 1, wherein said one or more conditioning scents are fragrances including at least one of anise, chamomile, lavender, tea tree, rose and vanilla.

10. The method, as claimed in claim 1, further including:
    increasing an amount of time between conditioning events, said conditioning events including said steps of repeatedly exposing the animal and conducting intermediate reinforcement.

11. The method, as claimed in claim 1, further including: increasing an amount of time between scent exposure and receipt of a reward within a scent-reward cycle.

* * * * *